(12) United States Patent
Witt (10) Patent No.: US 8,930,211 B2
(45) Date of Patent: Jan. 6, 2015

(54) METHOD OF OPERATING A MEDICAL DEVICE

(75) Inventor: Erik Kurt Witt, Murrysville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 515 days.

(21) Appl. No.: 12/745,361

(22) PCT Filed: Nov. 25, 2008

(86) PCT No.: PCT/IB2008/054939
§ 371 (c)(1),
(2), (4) Date: May 28, 2010

(87) PCT Pub. No.: WO2009/072030
PCT Pub. Date: Jun. 11, 2009

(65) Prior Publication Data
US 2010/0312575 A1    Dec. 9, 2010

Related U.S. Application Data

(60) Provisional application No. 60/992,128, filed on Dec. 4, 2007.

(51) Int. Cl.
  *G06F 19/00*    (2011.01)
  *G06Q 50/00*    (2012.01)
(52) U.S. Cl.
  USPC .................................................. 705/2; 705/3
(58) Field of Classification Search
  USPC ............................................................ 705/2
  See application file for complete search history.

(56) References Cited

U.S. PATENT DOCUMENTS

| | | |
|---|---|---|
| 5,044,362 A | 9/1991 | Younes |
| 5,107,830 A | 4/1992 | Younes |
| 5,148,802 A | 9/1992 | Sanders |
| 5,203,343 A | 4/1993 | Axe |
| 5,313,937 A | 5/1994 | Zdrojkowski |
| 5,433,193 A | 7/1995 | Sanders |
| 5,458,137 A | 10/1995 | Axe |
| 5,535,738 A | 7/1996 | Estes |
| 5,632,269 A | 5/1997 | Zdrojkowski |
| 5,645,053 A | 7/1997 | Remmers |
| 5,794,615 A | 8/1998 | Estes |
| 5,803,065 A | 9/1998 | Zdrojkowski |
| 6,029,664 A | 2/2000 | Zdrojkowski |
| 6,085,747 A | 7/2000 | Axe |
| 6,087,747 A | 7/2000 | Dhuler |
| 6,105,573 A | 8/2000 | Delaplane |
| 7,225,809 B1 | 6/2007 | Bowen |
| 2002/0077856 A1 * | 6/2002 | Pawlikowski et al. ............ 705/2 |
| 2004/0230457 A1 * | 11/2004 | Rosenbloom et al. ............ 705/2 |
| 2006/0095904 A1 | 5/2006 | Gardner |
| 2007/0038477 A1 | 2/2007 | Kelly |

FOREIGN PATENT DOCUMENTS

| | | |
|---|---|---|
| JP | 2005202645 A | 7/2005 |
| JP | 2006296477 A | 11/2006 |

\* cited by examiner

*Primary Examiner* — Hiep V Nguyen (57) ABSTRACT

A method of operating a medical device having a memory and a processor, wherein the memory is structured to store a number of operating routines, each of at least some of the number of operating routines being associated with a number of operating features of the medical device, and wherein the processor is adapted to execute a first one of the number of operating routines enabling a first set of operating features. The method comprises receiving an enablement code associated with a second operating routine, executing the second operating routing for a predetermined period responsive to receipt of the enablement code, wherein execution of the second operating routine enables a second set of operating features, and terminating execution of the second operating routine responsive to expiration of the predetermined period.

20 Claims, 5 Drawing Sheets

METHOD OF OPERATING A MEDICAL DEVICE

BACKGROUND OF THE INVENTION

1. Field of the Invention

The present invention pertains to the operation of an electronically controlled medical device. More particularly, the invention pertains to enabling one or more operating features of an electronically controlled medical device during a trial period and allowing a user to continue using the one or more operating features on a subscription basis.

2. Description of the Related Art

A wide variety of electronically controlled medical devices are known and used to provide an equally wide variety of medical services ranging from monitoring the condition of a patient to providing a medical treatment. A common feature of electronically controlled medical devices is that a microprocessor executes an operating routine which enables any number of the device's operating features.

Many electronically controlled medical devices are specifically designed and manufactured such that their processors execute a single operating routine each and every time the device is used. For example, the processor in a conventional pulse oximeter executes an operating routine which enables the pulse oximeter to monitor a patient's arterial oxygen concentration. As another example, the processor in a conventional electroencephalograph executes an operating routine which enables the electroencephalograph to monitor a patient's brain waves. The operating features provided by each of these devices do not change because the operating routine executed by each processor does not change over the life of the device.

For purposes of the present invention, the phrase "operating feature" refers to any functional capability of the medical device. This includes features that are determined or set at the time of manufacture and cannot be altered by the user. This also includes features of the medical device that can be set, selected, or adjusted by an authorized technician, caregiver, and/or user, among others. Examples of operating features of specific medical devices are discussed in greater detail below.

It can be appreciated that the need may arise to alter the operating routine and/or to upgrade the operating routine of a medical device after the manufacturing process is completed. For example, an operating routine may need to be altered to correct an error and/or an operating routine may need to be upgraded to take advantage of the latest technological advances developed after the device was released. U.S. Patent Application Publication No. 2002/0077856 to Pawlikowski et al., the entire contents of which are incorporated herein by reference, teaches a method and system for altering/upgrading one such type of electronically controlled medical device, a positive pressure therapy device.

For purposes of the present invention, the phases, "positive pressure therapy device", "therapy device", "pressure support system", and/or derivatives thereof, include any electronically controlled medical device or system, invasive or non-invasive, that delivers a flow of breathing gas to the airway of a patient (also referred to herein as a "user"). A positive pressure therapy device is typically used to treat a medical disorder, such as obstructive sleep apnea (OSA), congestive heart failure, and central sleep apnea, as well as other cardiorespiratory disorders. The positive pressure therapy device produces a flow of breathing gas at an elevated pressure which is delivered to a patient's airway via a patient circuit. The positive pressure therapy device may function in a number of modes, such as and without limitation, continuous positive airway pressure (CPAP) mode, bi-level pressure support mode, "auto-titration" mode, proportional assist ventilation (PAV) mode, and proportional positive airway pressure (PPAP) mode, each of which is discussed in more detail below.

The modes of operation, as well as the functions capable of being provided by the positive pressure therapy device in each mode, are typically determined at the time of manufacture. However, the specific mode in which the positive pressure therapy device is to selected to operate, the specific functions associated with the selected mode that are enabled, and the specific settings for a number of adjustable parameters of the selected mode are generally not set when the positive pressure therapy device leaves the factory. Instead, a dealer may select these items based on the needs of the user.

Some positive pressure therapy devices are manufactured to operate in a single pressure support mode. However, many conventional positive pressure therapy devices are manufactured with the capability of operating in multiple pressure support modes (such as, CPAP, bi-level, auto-titration, PPAP, PAV, or a combination thereof, among others). Accordingly, a manufacturer, supplier, or seller of medical devices is able to sell or lease a number of identical medical devices to a medical device provider or dealer. The medical device provider or dealer then enables and/or disables particular operating features of the medical devices prior to distributing the medical devices to the doctors' offices, hospitals, or directly to the users. For example, a manufacturer may produce a positive pressure therapy device capable of providing several pressure support modes (e.g., CPAP, bi-level, etc.). The dealer, upon receiving an order, can then enable the prescribed desired pressure support mode and the desired operating features associated with that mode and/or disable the un-prescribed pressure support mode and the operating features associated with those un-prescribed modes prior to distributing the device to the patient.

A dealer, for example, may have in stock from the manufacturer a positive pressure therapy device that is capable of providing CPAP, bi-level, and auto-titration modes of therapy. For a patient who is prescribed CPAP therapy as a treatment for OSA, the dealer enables the device to function in the CPAP mode prior to delivering the device. The other modes of therapy may are disabled. In this example, the CPAP mode may have a maximum pressure setting, a minimum pressure setting, a ramp time setting, and alarm settings (among other settings) associated therewith when shipped by the manufacturer to the dealer. The dealer, prior to delivering the device to the user, may enable only the maximum and minimum pressure settings and one or more alarm settings. The other alarm settings and the ramp time setting are disabled. The dealer may also set the device to deliver the supply of breathing gas to the user at the therapeutic level prescribed by the user's physician. The mode in which the positive pressure therapy device operates, the functions of the positive pressure therapy device associated with each mode, and the adjustable parameters associated with each mode are considered to be, without limitation, examples of the operating features of the positive pressure therapy device for present purposes.

In CPAP mode, the positive pressure therapy device supplies a flow of breathing gas at a constant positive pressure to the airway of a patient throughout the patient's breathing cycle. The ability of a positive pressure therapy device to provide a continuous pressure, as opposed, for example, to a variable pressure, is an operating feature of the system. The specific pressure at which the device is set to deliver the breathing gas (i.e., the therapeutic pressure) is another example of an operating feature of the system. Setting the therapeutic pressure is accomplished, for example, by manually setting a switch, dial, knob or other input device associated with the medical device.

For bi-level pressure support mode, the pressure of the breathing gas delivered to the patient varies in synchronization with the patient's breathing cycle. Generally, a lower pressure is delivered to the patient during the expiratory phase of the breathing cycle than is delivered during the inspiratory phase. As a result, the patient receives the necessary pressure support during inspiration to treat their disorder, such as OSA, but is not breathing out against a relatively high pressure during expiration. Bi-level pressure support provides increased comfort to some patients. With bi-level pressure support, the patient's inspiratory positive airway pressure (IPAP), expiratory positive airway pressure (EPAP), and how the device detects and compensates for system leaks, if any, are examples of operating features of the positive pressure therapy device. Bi-level pressure support is taught, for example, in U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., and U.S. Pat. No. 6,029,664 to Zdrojkowski et al., the entire contents of which are incorporated by reference into the present invention.

For auto-titration mode the pressure provided to the patient changes based on the detected conditions of the patient, such as whether the patient is snoring or experiencing an apnea, hypopnea, upper airway resistance, or a combination thereof. In this mode, the positive pressure therapy device itself determines the optimum pressure to deliver the flow of gas to the patient. If snoring or an apnea is detected, for example, the positive pressure therapy device increases the pressure of the gas delivered to the patient's airway. When the detected snoring or apnea ceases, the positive pressure therapy device decreases the pressure of the gas delivered to the patient's airway. With auto-titration mode, the operating features typically include, for example and without limitation, a maximum and/or minimum pressure that can be output by the device and the technique by which the system alters the patient pressure.

An example of an auto-titration positive pressure therapy device that adjusts the pressure delivered to the patient based on whether or not the patient is snoring is the Virtuoso® CPAP family of devices manufactured and distributed by Respironics, Inc. This auto-titration pressure support mode is taught in U.S. Pat. Nos. 5,203,343; 5,458,137 and 6,087,747 all to Axe et al., the entire contents of which are incorporated herein by reference. An example of a positive pressure therapy device that actively tests the patient's airway to determine whether obstruction, complete or partial, could occur and adjusts the pressure output to avoid this result is the Tranquility® Auto CPAP device, also manufactured and distributed by Respironics, Inc. This auto-titration pressure support mode is taught in U.S. Pat. No. 5,645,053 to Remmers et al., the entire content of which is incorporated herein by reference.

For PAV mode, the pressure of gas delivered to the patient varies with the patient's breathing effort to increase patient comfort. U.S. Pat. Nos. 5,044,362 and 5,107,830 both to Younes, the entire contents of which are incorporated herein by reference, teach a positive pressure therapy device capable of operating in a PAV mode. For PPAP mode, breathing gas is delivered to the user based on the flow generated by the user. U.S. Pat. Nos. 5,535,738; 5,794,615; and 6,105,573 all to Estes et al., the entire contents of which are incorporated herein by reference, teach a positive pressure therapy device capable of operating in a PPAP mode. The percentage of assistance provided by the device is at least one of the operating features of a positive pressure therapy device operating in the PAV or PPAP modes.

Other operating features for a positive pressure therapy device include, without limitation, alarm features, time backup breath features (a ventilatory breath delivered when a user fails to spontaneously initiate a breath within a set period of time), and a pressure ramp (the pressure level provided to the user is gradually increased over time). Activating, deactivating, or altering most features of the positive pressure therapy device is preferably and, in many cases, necessarily done by an authorized caregiver or technician under the direction and/or supervision of the physician or other caregiver responsible for that user.

In certain situations, medical reimbursement policies dictate that a patient be treated with the most basic operating features of a first type of pressure support mode before a reimbursement will be authorized for more advanced features of that type of pressure support mode and/or authorized for a second type of pressure support mode. For example, it is not uncommon for an OSA sufferer to initially be prescribed treatment with a CPAP device. The patient may then be switched to a bi-level device only after it is determined that CPAP therapy does not provide the desired therapy results. Under current reimbursement policies, a dealer only receives reimbursement for providing a CPAP device with the basic operating features enable. Thus, these reimbursement policies create a disincentive for the dealer to enable more advanced, un-prescribed operating features.

Because a patient only receives a device capable of providing the basic operating features associated with the prescribed pressure support mode, the patient may never experience the benefits related to more advanced operating features of that mode or the benefits related to operating features of a different pressure support mode. As a result, a patient finding their prescribed pressure support mode uncomfortable or ineffective may fail to comply with their prescribed therapy regimen. In many cases, patients are unaware that more advanced operating features or different pressure support modes even exist. Thus, such patients may never experience more advanced operating features or a different therapy even though these may provide a more comfortable and more effective treatment regiment to the patient.

Even if aware of the benefits of the more advanced operating features or other therapy mode, a patient may experience difficulty in having their device upgraded. For example, the patient may be required to return their device to the dealer or manufacturer to complete the upgrade. Additionally, the dealer may be reluctant to upgrade the device because of the disincentives created by the reimbursement policies.

Accordingly, a need exists for an improved system and method for providing a patient with the opportunity to experience a number of additional operating features of a medical device on a trial basis and for providing the patient the opportunity to upgrade his or her device with the additional operating features if so desired.

SUMMARY OF THE INVENTION

In accordance with an aspect of the present invention, a method of operating a medical device having a memory and a processor, wherein the memory is structured to store a number of operating routines, each of at least some of the number of operating routines being associated with a number of operating features of the medical device, and wherein the processor is adapted to execute a first one of the number of operating routines enabling a first set of operating features, comprises receiving an enablement code associated with a second operating routine; executing the second operating routing for a predetermined period responsive to receipt of the enablement code, wherein execution of the second operating routine enables a second set of operating features; and terminating execution of the second operating routine responsive to expiration of the predetermined period.

According to another aspect of the present invention, a method for enabling a number of operating features of a medical device comprises receiving information identifying the medical device; generating an enablement code associated with the identified medical device; and providing the enablement code to the identified medical device, wherein the medical device is adapted to enable the number of operating features for a predetermined time responsive to receipt of the enablement code.

According to another aspect of the present invention, a method for operating a medical device having a first set of operating features enabled comprises receiving an enablement code corresponding to a second set of operating features; enabling the second set of operating features responsive to receiving the enablement code; and disabling the second set of operating features responsive to expiration of a predetermined period.

According to another aspect of the present invention, a medical device comprises a memory device structured to store a number of operating routines, each of at least some of the number of operating routines being associated with a set of operating features of the medical device; a processor adapted to execute a first one of the number of operating routines enabling at least some of the first set of operating features; and an interface means adapted to communicate an enablement code to the processor, wherein in response to receiving the enablement code the processor is adapted to at least one of execute the first one of the number of operating routines enabling at least one other operating feature of the first set of operating features for a predetermined period; and execute a second one of the number of operating routines enabling at least some of a second set of operating features for a predetermined period.

According to another aspect of the present invention, a medical device comprises a storage means for storing a number of operating routines, each of at least some of the number of operating routines being associated with a set of operating features of the medical device; a processing means for executing a first one of the number of operating routines enabling at least some of the first set of operating features; and an interface means for communicating to the processing means an enablement code to the processing means, wherein in response to receiving the enablement code the processing means is adapted to at least one of execute the first one of the number of operating routines enabling at least one other operating feature of the first set of operating features for a predetermined period; and execute a second one of the number of operating routines enabling at least some of a second set of operating features for a predetermined period.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of "a", "an", and "the" include plural referents unless the context clearly indicates otherwise.

As employed herein, the statement that two or more parts are "connected", "coupled", or "attached" together shall mean that the parts are joined or operate together either directly or joined together through one or more intermediate parts.

As employed herein, the phrase "operating feature" refers to any functional capability of a medical device and the phrase "a set of operating features" shall mean a number of operating features.

The present invention generally relates to a system and method for operating an electronically controlled medical device. More specifically, the present invention relates to a medical device in which a set of operating features are enabled on a trial basis such that a user has the ability to experience the benefits provided by the set of operating features. After the trial period, the user may upgrade the device such that one or more of the operating features remain enabled.

It is contemplated that the present invention is applicable to any electronically controlled medical device. Accordingly, it is understood that the following discussion, which is generally directed to positive pressure therapy devices for ease of understanding, is in no way intended to limit the present invention to such positive pressure therapy devices.

As discussed above, a positive pressure therapy device is any medical device or system, invasive or non-invasive, that delivers a flow of breathing gas to the airway of a patient. Examples of positive pressure therapy devices include, without limitation, any of the M-Series positive pressure therapy devices manufactured and distributed by Respironics, Inc. of Murrysville, Pa.

A manufacturer may offer several different models of therapy devices in their product portfolio. Typically, a manufacturer employs a standard hardware and/or software platform capable of supporting a number of operating features. To differentiate between the different models of therapy devices, particular hardware and/or software components may be turned on or off such that each model is provides a particular set of operating features. Some operating features, however, may require additional hardware and/or software components or better-performing components. It may be advantageous for the manufacturer to include but deactivate (or not use) the additional or better performing components, for example, if there is the potential for collecting payment from a user in response to activating the additional feature at a later time.

A patient is typically prescribed a positive pressure therapy device to treat a medical disorder, such as obstructive sleep apnea (OSA), congestive heart failure, and central sleep apnea, as well as other cardio-respiratory disorders. Generally, the patient receives a device having only the basic operating features enabled. The device's more advanced features are typically disabled when the device is delivered to the patient. The patient, however, may be made aware of the benefits that these advanced operating features could provide should they be enabled. The patient is notified that these benefits can be experienced at not cost during a trial period. If the patient wishes to experience these benefits, the patient requests and receives a trial enablement code from, for example, the device manufacturer. In response to the receiving the trial enablement code, the positive pressure therapy device executes an associated operating routine which enables a set of operating features for a trial period. The trial period can be based on any measurement factor, such as and without limitation, hours of operation, therapy nights, or calendar days, among others.

After the trial period, the patient can continue to experience the benefits provided by one or more of these operating features by purchasing a subscription enablement code. In response to receiving the subscription enablement code, the positive pressure therapy device executes an associated operating routine which enables the one or more operating features for a subscription period. The subscription period can be based on any measurement factor, such as and without limitation, hours of operation, therapy nights, and calendar days, among others.

In one embodiment, for example, the trial period is based on hours of operation and the subscription period is based on calendar days. For example, the length of the trial period is set at 48 hours (i.e., once the trial period begins, the set of operating features remain enabled until the device accumulates 48 hours of operation); whereas the subscription period is set at one calendar year (i.e., the associated set of operating features are enabled for 365 days beginning when the subscription is activated). It should be noted that the length of the trial period and the length of the subscription period can be altered while remaining within the scope of the present invention. For example, the subscription period may be based on the therapy device's lifespan. In effect, the patient pays a one time fee and the one or more operating features are permanently enabled.

As an alternative to purchasing the subscription enablement code separately, the subscription enablement code can be provided to the patient in combination with the purchase of a related or accessory product. For example, many manufacturers recommend that a patient replace their patient interface device (e.g., mask) every six months. When the patient purchases the replacement mask, an associated subscription enablement code (which enables one or more operating features of the patient's therapy device) is also provided. In this example, the subscription period can be based on the life expectancy of the replacement patient interface. As such, the subscription period expires around the same time that the patient should purchase their next replacement mask. Thus, the patient is given another reminder/incentive to purchase their next replacement mask at the recommended interval.

Figure 1:
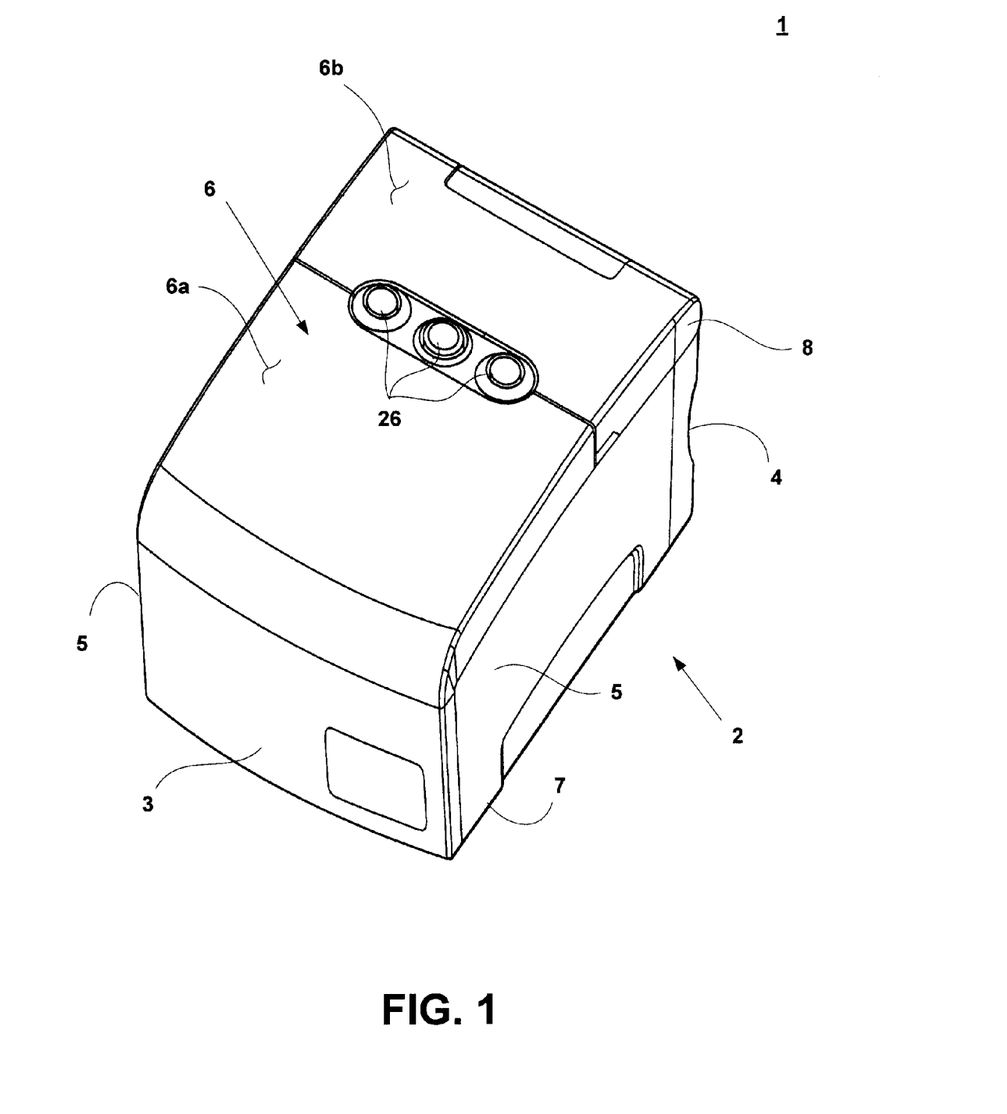
FIG. 1 is a perspective view of a positive pressure therapy device adapted to provide a regimen of respiratory therapy according to one embodiment of the present invention.

A perspective view of a positive pressure therapy device 1, adapted to provide a regimen of respiratory therapy to a patient, is generally shown in FIG. 1. The positive pressure therapy device 1 includes a housing 2 having a front wall 3 coupled to a rear wall 4 by two side walls 5 and a top 6, all of which are connected to a base 7. An interface device 26, here a number of buttons, is disposed on top 6. Top 6 includes a stationary portion 6a and a movable portion 6b. Movable portion 6b is connected to rear wall 4 by a hinge 8. Movable portion 6b is rotated about hinge 8 to reveal a number of additional interface devices (such as an LCD screen, switches, etc.; none of which are shown in FIG. 1). Rear wall 4 includes a first opening (not shown) adapted to allow a supply of gas to be communicated to a pressure generator contained within housing 2. Rear wall 4 also includes a second opening (not shown) adapted to allow pressurized gas to be delivered from the pressure generator to a patient circuit (not shown). Although not shown in FIG. 1, it is contemplated that the positive pressure therapy device 1 may include other components, such as and without limitation a humidifier, while remaining within the scope of the present invention.

Figure 2:
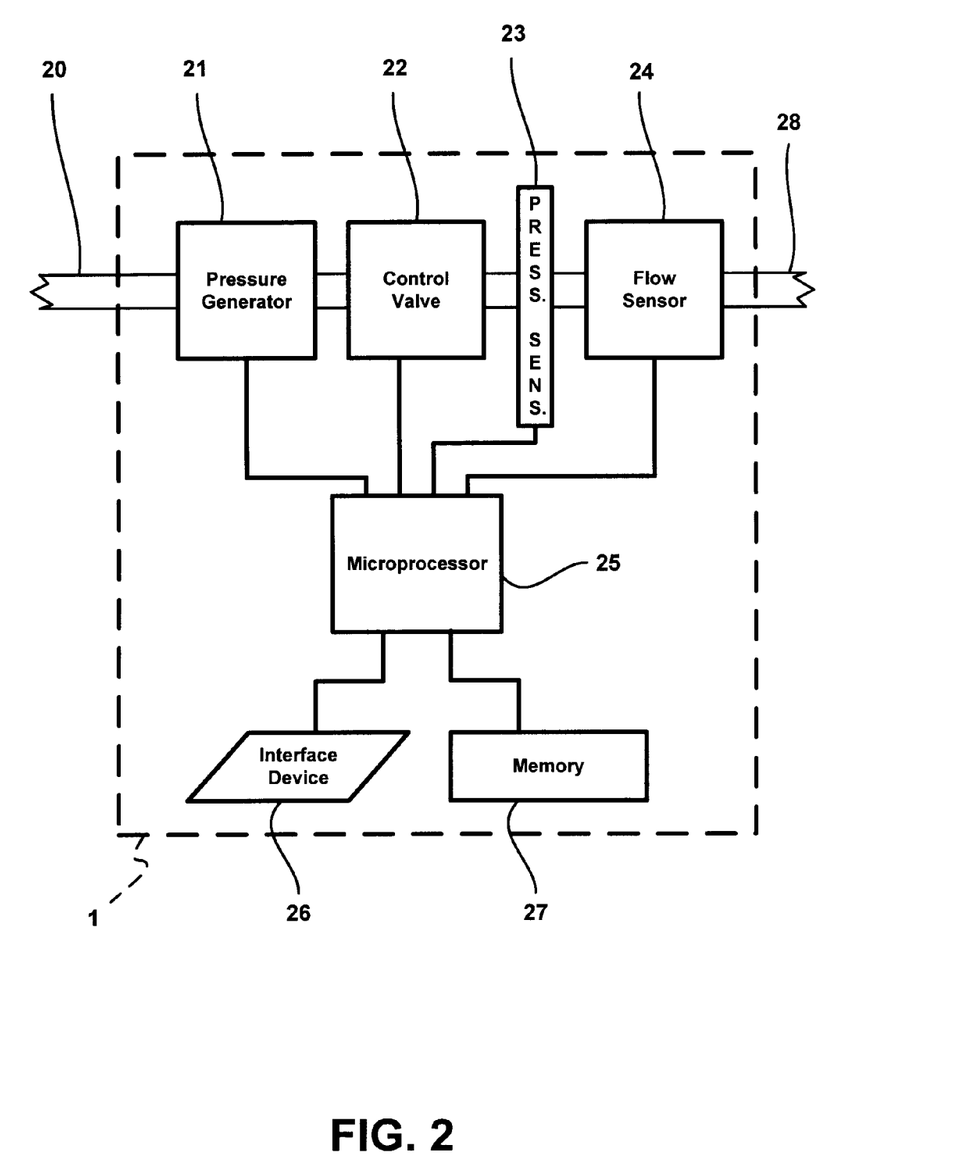
FIG. 2 is a schematic view of the positive pressure therapy device of FIG. 1 according to one embodiment of the present invention.

Referring now to FIG. 2, positive pressure support device 1 is a pressure generating system that receives a breathing gas from a breathing gas source (such as ambient atmosphere in the illustrated embodiment) and creates a flow of breathing gas at a pressure greater than the pressure of the supply of breathing gas (here, greater than ambient atmospheric pressure). The breathing gas is communicated from inlet 20 to a pressure generator 21, which elevates the pressure of the breathing gas, and then communicates the breathing gas to an outlet 28. The flow of breathing gas is then communicated from outlet 28 to a patient circuit (not shown). The patient circuit generally includes a patient interface device which facilitates delivery of the flow of breathing gas to the airway of a patient.

In an exemplary embodiment, pressure generator 21 is a centrifugal blower in which a fan or impeller is driven by a motor operating under the control of a processor 25. It is to be understood, however, that the present invention contemplates other techniques for generating a flow of breathing gas at an elevated pressure. For example, a drag compressor, fan, piston, or bellows, can also be used as pressure generator 21 in the positive pressure support device 1 to create the flow of breathing gas at a pressure greater than the ambient atmospheric pressure.

The amount of flow and/or pressure of the breathing gas delivered to the patient can be regulated using a pressure controller. In the current embodiment, the pressure controller is a control valve 22 which is structured to exhaust a portion of the breathing gas to atmosphere or back to the low pressure side of pressure generator 21, restrict the flow of breathing gas through outlet 28, or perform a combination of these two functions. Processor 25 preferably directs the operation of control valve 22 to regulate the pressure or flow of breathing gas provided to the patient. Examples of suitable pressure controllers are taught in U.S. Pat. No. 5,694,923 to Hete et al. and U.S. Pat. No. 5,598,838 to Servidio et al.

It is also known to control the speed of a motor driving pressure generator 21 so that pressure generator 21 outputs the breathing gas at the desired flow or pressure. This motor speed control technique can be used alone, or it can be used in combination with a pressure controller, such as those discussed above, to control the flow or pressure of the breathing gas provided to the patient.

Positive pressure therapy device 1 also include a number of sensors adapted for measuring: a characteristic associated with the flow of breathing gas; the pressure of the breathing gas; a condition of a patient using the positive pressure therapy device 1; a condition of the positive pressure therapy device 1; or any combination thereof. FIG. 2, for example, schematically illustrates a flow sensor 24 and a pressure sensor 23, each of which is associated with outlet 28.

The output from such sensors are provided to processor 25 and, depending on the operating mode of positive pressure therapy device 1, are used to control the rate of flow and/or pressure of the breathing gas delivered to the patient. For example, changes in the patient's breathing cycle that are detected by such sensors are employed to initiate cycling from IPAP to EPAP and triggering from EPAP to IPAP in a positive pressure therapy device providing bi-level pressure support. As another example, the output of one or more such sensors is used to determine when to raise and lower the pressure provided to the patient, and is used to determine the magnitude of the change in pressure, in a positive pressure therapy device providing auto-titration pressure support. U.S. Pat. No. 5,645,053 to Remmers et al., the content of which is again incorporated herein by reference, provides one method of monitoring patient flow to determine when and how to adjust the pressure applied to the patient.

It should be noted that the location and number of such sensors can be different than that shown in FIG. 2, so long as the function of providing feedback for the control of the positive pressure therapy device is achieved. In addition, it is known to monitor the operation of the pressure generator 21 to determine the condition of the patient, such as whether the patient is breathing on the system. In which case, the functions of the pressure and/or flow sensors are effectively incorporated into the pressure generator monitoring function.

Although FIG. 2 illustrates the use of flow sensor 24 and pressure sensor 23, it is to be understood that other types of sensors can be used in positive pressure therapy device 1. For example, a microphone can be provided to detect sounds produced by the patient, which can be used, for example, in a positive pressure therapy device providing auto-titration pressure support to control the pressure of the breathing gas delivered to the patient. See, e.g., U.S. Pat. Nos. 5,203,343 and 5,458,137 both to Axe et al., the contents of which are again incorporated herein by reference.

Processor 25 is adapted to implement and/or execute a number of operating routines. The operating routines may be in any of a variety of forms such as, without limitation, software, firmware, and the like which are executable by processor 25. In the current embodiment, the operating routines are generally stored within memory 27 which is in operable communication with processor 25.

Each of at least some of the operating routines is associated with different sets of operating features of the therapy device. For example, a first operating routine when executed by processor 25 may cause the positive pressure therapy device 1 to operate in a continuous positive air pressure (CPAP) mode. Execution of the first operating routine may also establish certain parameters within that mode, such as and without limitation, a minimum output pressure limit, a maximum output pressure limit, and a therapeutic pressure. The particular mode of operation and the particular parameters of operation within that mode are examples of operating features associated with the first operating routine.

Execution of another operating routine generally enables a different set of operating features. For example, a second operating routine when executed by processor 25 may cause the positive pressure therapy device 1 to operate in a bi-level positive air pressure therapy mode. Execution of the second operating routine may also establish certain parameters within that mode, such as and without limitation, an inspiratory positive airway pressure (IPAP), an expiratory positive airway pressure (EPAP), leak detection, and leak compensation.

Processor 25 is capable of executing a single routine or simultaneously executing any number of routines. For example, because the first and second operating routines discussed above are associated with different therapy modes (i.e., CPAP and bi-level), processor 25 may suspend execution of the first operating routine prior to initiating execution of the second operating routine, and vice versa. A third operating routine, however, when executed by processor 25 may enable within the CPAP mode operating features corresponding to a pressure relief therapy adapted to reduce the pressure of the breathing gas delivered to the patient at the beginning of exhalation and to return the pressure of the breathing gas to the therapeutic pressure just prior inhalation. Thus, it is contemplated that processor 25 would simultaneously execute the first operating routine, which causes the positive pressure therapy device 1 to operate in CPAP mode, and the third operating routine, which enables the pressure relief therapy feature. In this example, the third operating routine functions like a sub-routine of the first operating routine.

Memory 27 provides storage for, among others, the number of routines executable by processor 25. Memory 27 can be any of a variety of types of internal and/or external storage media such as, without limitation, RAM, ROM, EPROM(s), EEPROMS(s), and the like that provide a register for data storage such as in the fashion of an internal storage area of a computer, and can be volatile memory or nonvolatile memory.

In the illustrated exemplary embodiment, positive pressure therapy device 1 includes an interface device 26 structured to exchange information between positive pressure therapy device 1 and, for instance, a user. Examples of interface devices 26 include the manually actuated buttons provided on housing 2, displays, keypads, voice activated input devices, audio outputs, indicators (e.g., lights), switches, knobs, modems, and networking cards, among others.

Although the positive pressure therapy device 1 is discussed above in conjunction with a specific arrangement of components, it is contemplated that other arrangements, components, and/or combinations may be used to generate a flow of breathing gas within the scope of the present invention.

Due to the current reimbursement policies, it is common for a medical device to be delivered to the user with one or more advanced operating features disabled. In the accordance with the principles of the present invention, the user is made aware that such advanced operating features are available and can be enabled for a trial period and/or for a subscription period.

For example, a user may receive a REMstar® Pro M Series positive pressure therapy device manufactured and distributed by Respironics, Inc. of Murrysville, Pa.). The REMstar® Pro M Series positive pressure therapy device is capable of delivering the C-Flex™ waveform, a pressure relief feature. Due to the reimbursement policies, however, the dealer may deliver this device to the user with the C-Flex™ pressure relief feature disabled. The dealer provides literature to the user which explains the functionality and the comfort benefits of the C-Flex™ pressure relief feature, as well as the health benefits from the demonstrated increase in compliance resulting from activation and use of the C-Flex™ pressure relief feature. The literature explains that the C-Flex™ pressure relief feature can be tried on a trial basis and further provides contact information (e.g., a telephone number, website address, etc.) for obtaining a trial enablement code. Alternatively, the device may be adapted to notify the user of the benefits of using the C-Flex™ pressure relief feature. For instance, a notification message can be periodically displayed on the device's LCD screen.

Figure 3:
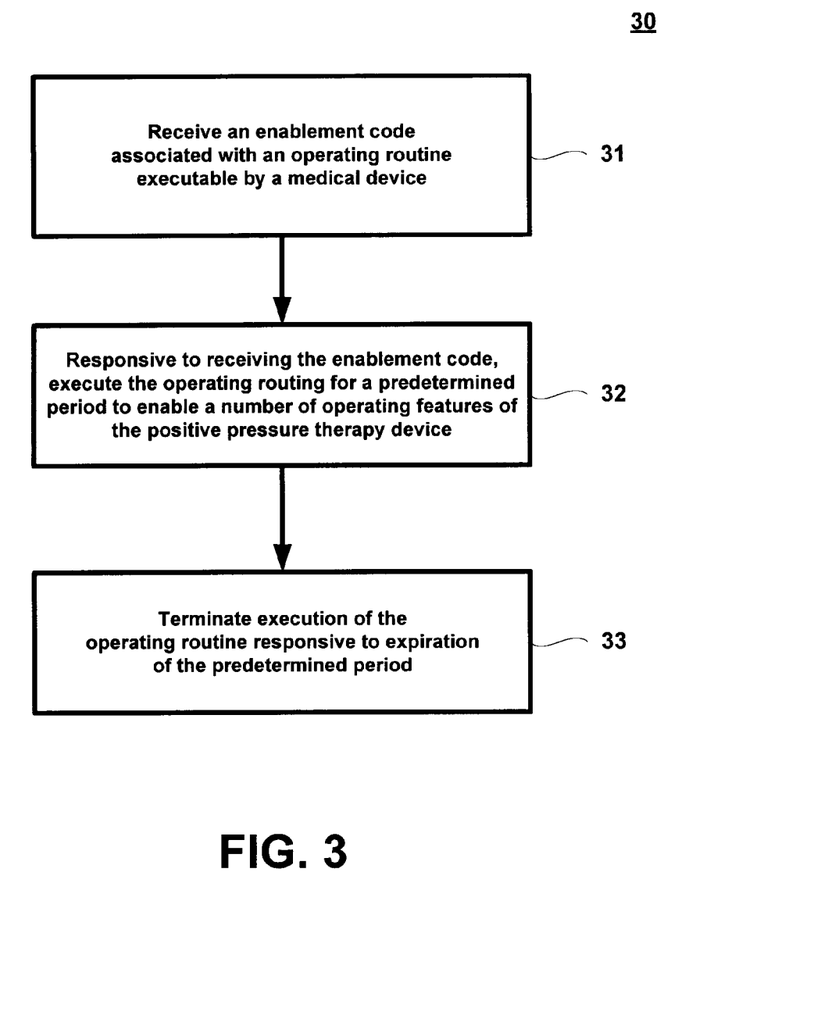
FIG. 3 is a flowchart illustrating a process for operating a medical device according to one embodiment of the present invention.

FIG. 3 illustrates an operational process 30 for operating a medical device according to the principles of the present invention. In the current embodiment, operational process 30 is implemented to enable a number of operating features of a positive pressure therapy device (such as the positive pressure therapy device 1 illustrated in FIGS. 1 and 2).

Operational process 30 is initiated at operation 31 where an enablement code is received by the medical device. In the current embodiment, a patient obtains the enablement code from the manufacturer of the device and enters the enablement code into the medical device. For example, the patient has a positive pressure therapy device 1 capable of providing CPAP therapy with a pressure relief technology (such as the REMstar® Pro M Series with C-Flex™ pressure relief feature discussed above). However, one or more operating features, such as the pressure relief feature, are disabled by the manufacturer prior to shipping the positive pressure therapy device 1.

In the current embodiment, the patient contacts the manufacturer to request a trial enablement code. The patient is required to supply certain information about the positive pressure therapy device 1 to the manufacturer, such as and without limitation the serial and model number of the device. This information is used to generate a trial enablement code unique to the patient's positive pressure therapy device 1 so that the trial enablement code cannot be used to enable a set of operating features for another device. The trial enablement code corresponds to an operating routine that is associated with an operating feature of the device and, among other things, establishes the length of the trial period.

The manufacturer conveys the trial enablement code to the patient or directly to the pressure therapy device in any suitable manner (e.g., electronically, orally, physically, etc.). For example, the enablement code can be sent to the patient on a smart card. The patient inserts the smart card into a smart card reader associated with the therapy device and downloads the enablement code. As another example, the enablement code is conveyed to the patient over the telephone and the patient enters the enablement code into the therapy device using a keyboard and/or input buttons. As yet another example, the enablement code is electronically transmitted directly to the therapy device via a modem or networking card. Generally, an enablement code corresponds to an operating routine already stored in the memory of the device, however, it is contemplated that a corresponding operating routine can be loaded into the device at or about the same time that the enablement code is conveyed to the device.

After the enablement code is received by the positive pressure therapy device 1, operational control then passes to operation 32 where, responsive to receiving the enablement code, the associated operating routine is executed for a predetermined period. As a result, a number of operating features associated with the enablement code are enabled. Continuing with the example above, processor 25 executes the operating routine associated with the trial enablement code and enables the set of operating features associated with the pressure relief technology. This set of operating features remains enabled for the trial period. Once enabled, in the current embodiment, the patient is able to toggle the set of operating features related to the pressure relief technology on and off. Thus, the patient is better able compare the benefits provided by the positive pressure therapy device 1. For example, the patient may begin therapy with the pressure relief feature toggled "on" and note how comfortable the therapy provided the device feels. The patient can then toggle the pressure relief feature "off" and note the difference in the comfort level. Once the trial period expires, however, the pressure relief feature is disabled and the patient can no longer toggle the pressure relief feature "on".

After the operating routing related to the enablement code is executed, operational control then passes to operation 33 where, the execution of the operating routine is terminated after the predetermined period expires. Once execution of the operating routine is terminated, the operating features related to that operating routing are disabled. In the current embodiment, processor 25 is adapted to maintain a timer or counter to determine when the trial period expires. Upon expiration of the trial period, processor 25 terminates execution of the operating routine related to the trial enablement code; thus disabling the operating features associated with that operating routine. Processor 25 then reinitiates execution of the operating routine that was being executed prior to receiving the trial enablement code. In the current example, the pressure relief feature is disabled and the therapy device provides the basic CPAP features.

Although the current embodiment was discussed in the context of a trial enablement code, it is contemplated that operational process 30 can also be used in relation to a subscription enablement code. In one embodiment, the manufacturer provides a trial enablement code to the patient at no cost. The manufacturer then offers for sale to the patient a subscription enablement code. In another embodiment, the subscription enablement code is provided to the patient in combination with the purchase of a related or accessory product, such as a patient interface. Furthermore, although discussed in context of the manufacturer supplying the enablement code to the patient in the current embodiment, it is contemplated that operational process 30 may entail some other entity or entities (such as and without limitation, a supplier, a seller, a provider or a dealer). For example, a dealer may supply the enablement code to the patient.

Figure 4:
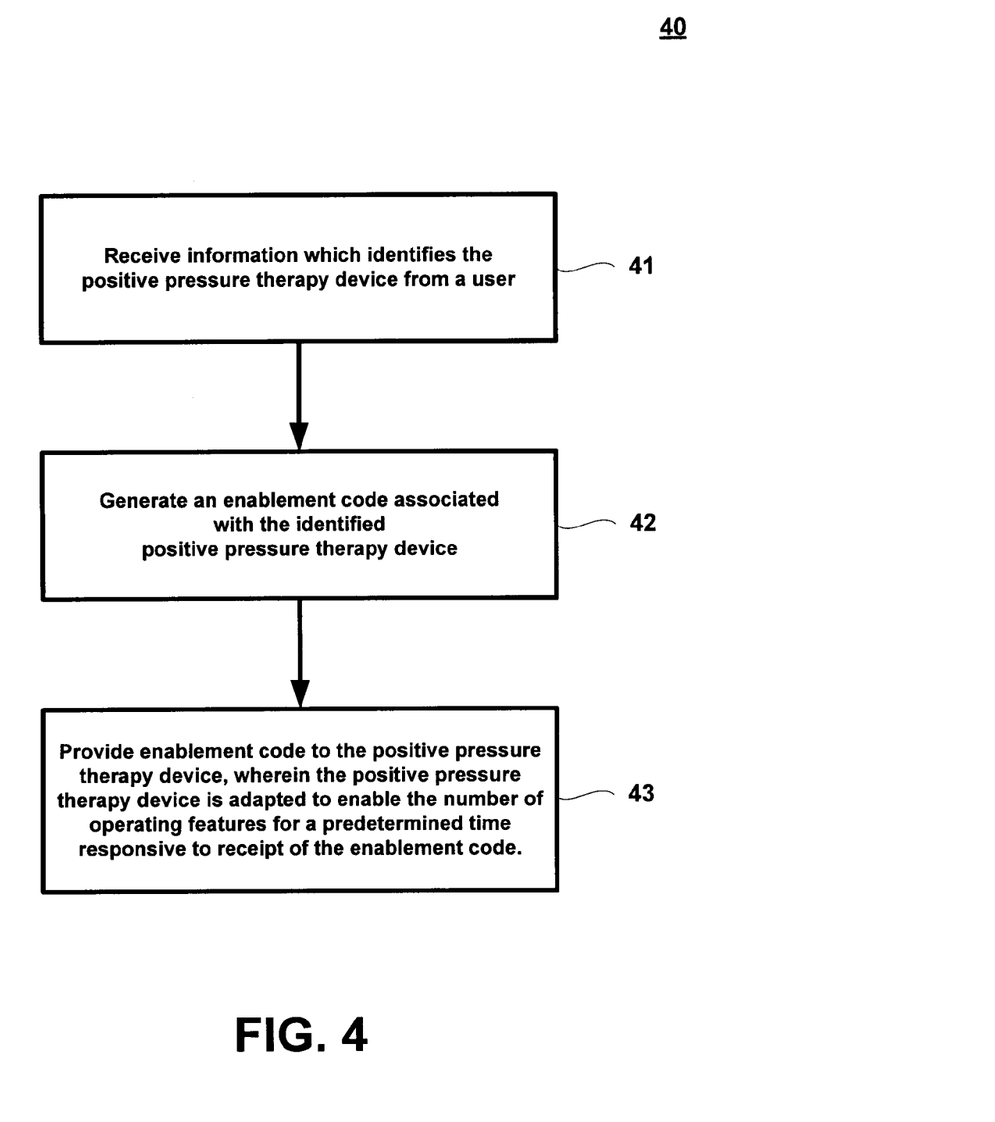
FIG. 4 is a flowchart illustrating a process for enabling operating features of a medical device according to one embodiment of the present invention.

FIG. 4 illustrates an operational process 40 for enabling a number of operating features of a medical device according to the principles of the present invention. In the current embodiment, operational process 40 is implemented by a manufacturer in response to a request from a patient; however, it is contemplated that operational process 40 can be implemented by other entities while remaining within the scope of the present invention. For example and without limitation, operational process 40 may be implemented by a supplier or seller in response to a request from a provider or dealer.

Operational process 40 is initiated at operation 41 where information which identifies the medical device is received. In the current embodiment, the manufacturer of a positive pressure therapy device 1 receives, from a patient, information that identifies a positive pressure therapy device 1 such as the serial and/or model number.

After identifying information is received, operational control passes to operation 42, where an enablement code associated with the medical device is generated. In the current embodiment, the manufacturer generates an enablement code associated with the positive pressure therapy device 1 identified by the information provided by the patient.

After the enablement code is generated, operational control passes to operation 43 where the enablement code is conveyed the medical device. In the current embodiment, the manufacturer conveys the enablement code to the patient who then enters the enablement code into the positive pressure therapy device 1. Alternatively, the enablement code can be conveyed directly to the positive pressure therapy device 1 (e.g., via modem, networking card, etc.). In response to receiving the enablement code, the positive pressure therapy device 1 is adapted to execute an operating routine which enables a number of operating features for a predetermined time associated with the enablement code.

Although operational process 40 is discussed in conjunction with a transaction between the manufacturer and the patient, it is contemplated that other parties may be substituted or added while remaining within the scope of the present invention. For example, it is contemplated that the patient provides information identifying the medical device to the dealer. And that the dealer generates the enablement code. As another example, it is contemplated that the dealer provides information identifying the medical device to the manufacturer and that the manufacturer generates and conveys the enablement code to the dealer who then enters the enablement code into the device. It is also contemplated that one or more intermediaries may be used while remaining within the scope of the present invention. For example, it is contemplated that the patient provides the identifying information to the dealer, who in turn provides the information to the manufacturer. The manufacturer generates and conveys the enablement code to the dealer who in turn conveys the enablement code to the patient.

Figure 5:
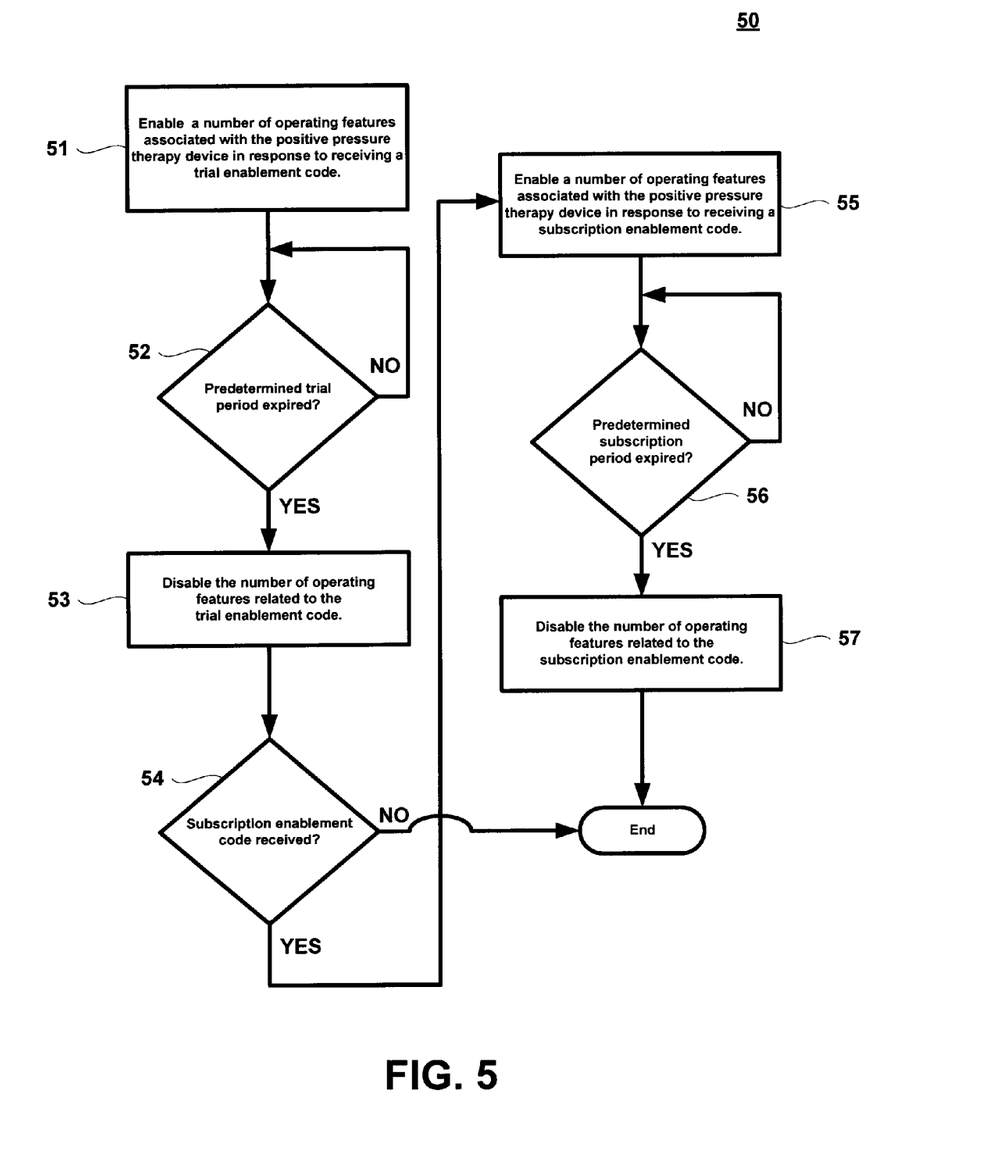
FIG. 5 is a flowchart illustrating a process for enabling operating features of a medical device according to one embodiment of the present invention.

FIG. 5 is a flowchart illustrating an operational process 50 for enabling operating features of the positive pressure therapy device according to another embodiment of the present invention. Operational process 50 is initiated at operation 51 where a number of operating features associated with a medical device are enabled in response to receiving a trial enablement code. In the current embodiment, operational process 50 is implemented on a positive pressure therapy device, such as a positive pressure therapy device 1 which is capable of providing CPAP therapy with a pressure relief technology (such as the REMstar® Pro M Series with C-Flex™ pressure relief feature discussed above). One or more operating features, however, such as the pressure relief feature and a ramp feature, are disabled by the manufacturer prior to shipping the positive pressure therapy device 1. At operation 51, the pressure relief and the ramp features are associated with the trial enablement code and are enabled in response to receipt of the trial enablement code by the positive pressure therapy device.

After the operating features associated with the trial enablement code are enabled at operation 51, operational control passes to operation 52 where a determination is made as to whether the trial period has expired. In the current embodiment, the length of the trial period is associated with the trial enablement code. The amount of the trial period that has elapsed is monitored by processor 25. If the trial period has not expired, operation 52 branches "NO" and operational control loops back to operation 52. If the trial period has expired, operation 52 branches "YES" and operational control is passed to operation 53.

At operation 53, the operating features related to the trial enablement code are disabled. In the current embodiment, for example, the pressure relief feature and the ramp feature that were enabled at operation 51 are disabled. Operational control is then passed to operation 54.

At operation 54, a determination is made as to whether a subscription enablement code has been received. If a subscription enablement code is not received, operation 54 branches "NO" and operational control is passed to operation 58 which terminates operational process 50. If a subscription enablement code is received, operation 54 branches "YES" and operational control is passed to operation 55.

In the current embodiment, a subscription enablement code is generated and conveyed to the patient in the following manner. First, the patient supplies the manufacturer with information that identifies the patient's positive pressure therapy device and that identifies those operating features for which he/she would like to subscribe. For example, the patient in the current embodiment may wish to subscribe to the pressure relief feature, but not to the ramp feature. After receiving all of the necessary information, the manufacturer generates a subscription enablement code which is associated with the patient's device, which is associated with a subscription period, and which is associated with the pressure relief feature desired by the patient. Before conveying the subscription enablement code, the manufacturer may require the patient to remit payment. The manufacturer then conveys the subscription enablement code for the identified device after receipt of the patient's payment.

In an alternative embodiment, the subscription enablement code is provided to the patient in combination with the purchase of a related or accessory product. For example, many manufacturers recommend that a patient replace their patient interface device (e.g., mask) every six months. When the patient purchases the replacement mask, an associated subscription enablement code (which enables one or more operating features of the patient's therapy device) is also provided. In this example, the subscription period can be based on the life expectancy of the replacement patient interface. As such, the subscription period expires around the same time that the patient should purchase their next replacement mask. Thus, the patient is given another reminder/incentive to purchase their next replacement mask at the recommended interval.

As stated above, if a subscription enablement code is received, control is passed to operation 55 where the operating features associated with the subscription enablement code are enabled. In the current embodiment for example, the pressure relief feature is enabled in response to receiving the subscription enablement code.

After the operating features associated with the subscription enablement code are enabled at operation 55, operational control is passed to operation 56 where a determination is made as to whether the subscription period has expired. If the subscription period has not expired, operation 56 determines "NO" and operational control loops back to operation 56. If the trial period has expired, operation 56 determines "YES" and operational control is passed to operation 57 where the operating features associated with the subscription enablement code are disabled.

After the operating features associated with the subscription enablement code are disabled at operation 57, operational control is passed to operation 58 where operational process 50 is terminated.

It should be noted that the original operating features of the medical device may remain enabled whether the operating features associated with the trial enablement code and/or the subscription enablement code are enabled or disabled. Furthermore, the original operating features of the medical device which are disabled when the operating features associated with the trial enablement code and/or the subscription enablement code are enabled, are re-enable when the operating features associated with the trial enablement code and/or the subscription enablement code are disabled. In other words, the device provides to the patient at least the same operating features that were enabled prior to receipt of the trial enablement code and/or the subscription enablement code.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A method of operating a medical device having a memory and a processor, the method comprising acts of:
    ab initio storing in the memory first and second pluralities of operating routines respectively associated with first and second operating features of the medical device to provide a therapy, the first and second plurality of operating routines being respectively associated with different modes of operation of the medical device;
    executing the first plurality of operating routines while maintaining the second plurality of operating routines disabled;
    receiving an enablement code indicating a predetermined period for permitting execution of the second plurality of operating routines by the medical device;
    executing the second plurality of operating routines for the predetermined period responsive to the receipt of the enablement code; and
    disabling the execution of the second plurality of operating routines at expiration of the predetermined period.

2. The method of claim 1, further comprising acts of:
    suspending execution of the first plurality of operating routines while the second plurality of operating routines is being executed; and
    reinitiating execution of the first plurality of operating routines expiration of the predetermined period.

3. The method of claim 1, further comprising an act of verifying that the enablement code is authorized for use with the medical device.

4. The method of claim 1, wherein the enablement code comprises a trial enablement code and the predetermined period comprises a trial period.

5. The method of claim 1, wherein the enablement code comprises a subscription enablement code and the predetermined period comprises a subscription enablement period.

6. A method for enabling operating features of a medical device having a memory and a processor, the method comprising acts of:
    ab initio storing in the memory first and second pluralities of operating routines respectively associated with first and second operating features of the medical device to provide a therapy, the first and second plurality of operating routines are respectively associated with first and second modes of operation of the medical device;
    receiving information identifying the medical device;
    generating an enablement code associated with the identified medical device and one of the first and second modes, the enablement code having associated therewith a predetermined period for execution of the second operating features by the medical device;
    providing the enablement code to the identified medical device;
    executing the first operating features while maintaining the second operating features disabled;
    executing the second operating features for the predetermined period responsive to receipt of the enablement code, and
    terminating the execution of the second operating features at expiration of the predetermined period.

7. A method for operating a medical device, the medical device having a memory and a processor, the method comprising acts of:
    ab initio storing in the memory first and second pluralities of operating routines respectively associated with first and second operating features of the medical device to provide a therapy, the first and second plurality of operating routines being respectively associated with different modes of operation of the medical device;
    executing the first plurality of operating routines while maintaining the second plurality of operating routines disabled;
    receiving an enablement code indicating a predetermined period for permitting execution of the second plurality of operating routines by the medical device;
    executing enabling the second plurality of operating routines responsive to receiving the enablement code; and
    disabling the execution of the second plurality of operating routines at expiration of the predetermined period.

8. The method of claim 7, further comprising acts of:
    disabling the first plurality of operating routines responsive to receiving the enablement code; and
    re-enabling the first plurality of operating routines expiration of the predetermined period.

9. The method of claim 7, wherein receiving an enablement code, comprises acts of:
    identifying the medical device; and
    generating an enablement code uniquely associated with the medical device and the second plurality of operating routines.

10. A medical device, comprising:
    memory to store ab initio first and second pluralities of operating routines respectively associated with first and second operating features of the medical device to provide a therapy, the first and second pluralities of operating routines being respectively associated with different modes of operation of the medical device;
    a processor adapted to execute
        the first plurality of operating routines while maintaining the second plurality of operating routines disabled, and
        the second plurality of operating routines for duration of the predetermined period responsive to receipt of the enablement code; and
    an interface device adapted to communicate the enablement code to the processor, the enablement code triggering the processor to execute the second plurality of operating routines, the enablement code indicating the predetermined period for per min the execution of the second plurality of operating features by the medical device.

11. The medical device of claim 10, wherein the medical device is a positive pressure therapy device structured to generate a flow of positive pressure gas.

12. The medical device of claim 10, wherein the processor is adapted to disable the at least one operating feature of the first plurality of operating routines at expiration of the predetermined period.

13. The medical device of claim 10, wherein the processor is adapted to terminate execution of the second plurality of operating routines at expiration of the predetermined period.

14. The medical device of claim 10, wherein the processor is adapted to suspend execution of the first plurality of operating routines while executing the second plurality of operating routines and to reinitiate execution of the first plurality of operating routines at expiration of the predetermined period.

15. The medical device of claim 10, wherein the enablement code is one of a trial enablement code associated with a predetermined trial period and a subscription enablement code associated with a predetermined subscription period.

16. A medical device, comprising:
a storage for storing ab initio first and second pluralities of operating routines, respectively associated with first and second operating features of the medical device to provide a therapy, the first and second pluralities of operating routines being respectively associated with different modes of operation of the medical device;
a processor for executing
the first plurality of operating routines while maintaining the second plurality of operating routines disabled, and
enable execution of the second plurality of operating routines for duration of the predetermined period responsive to receipt of the enablement code; and
an interface for communicating the enablement code to the processor, the enablement code triggering the processor to execute the second plurality of operating routines, the enablement code indicating the predetermined period for permitting the execution of the second plurality of operating features by the medical device.

17. The medical device of claim 16, wherein the medical device is a positive pressure therapy device structured to generate a flow of positive pressure gas.

18. The medical device of claim 16, wherein the processor is adapted to disable the at least one operating feature of the basic operating features at expiration of the predetermined period.

19. The medical device of claim 16, wherein the processor is adapted to terminate execution of the second plurality of operating routines at expiration of the predetermined period.

20. The medical device of claim 16, wherein the processor is adapted to suspend execution of the first plurality of operating routines while executing the second plurality of operating routines and to reinitiate execution of the first plurality of operating routines at expiration of the predetermined period.

* * * * *